United States Patent [19]

Yamaguchi et al.

[11] Patent Number: 4,559,964
[45] Date of Patent: Dec. 24, 1985

[54] VALVE UNIT FOR A WASHING DEVICE OF PRIVATE PARTS OF HUMAN BODY

[75] Inventors: Yuji Yamaguchi; Shinji Kawai, both of Kariya, Japan

[73] Assignee: Aisin Seiki Kabushiki Kaisha, Kariya, Japan

[21] Appl. No.: 647,634

[22] Filed: Sep. 6, 1984

[30] Foreign Application Priority Data

Sep. 27, 1983 [JP] Japan ............................ 58-149469[U]
Sep. 29, 1983 [JP] Japan ............................ 58-150860[U]

[51] Int. Cl.⁴ .............................................. A47K 7/00
[52] U.S. Cl. .................................... 137/107; 137/599; 137/218; 4/448
[58] Field of Search ............... 137/107, 102, 596, 599, 137/218; 4/443, 448

[56] References Cited

U.S. PATENT DOCUMENTS

| 1,015,653 | 1/1912 | Szczyglinski | 137/107 |
| 3,027,907 | 4/1962 | Lee | 137/107 |
| 4,287,618 | 9/1981 | Silver | 4/443 |

Primary Examiner—Alan Cohan
Attorney, Agent, or Firm—Oblon, Fisher, Spivak, McClelland & Maier

[57] ABSTRACT

A water flow control valve unit for a washing device of the private parts of a human body using a nozzle spouting water, in which several valves necessary for controlling the water flow to the nozzle are arranged unitedly as a single unit. The changeover valve in the unit has a plurality of longitudinal holes for passing through water and a diaphragm which opens only when water passes through the holes, whereby the water pressure given to the nozzle is maintained at a degree sufficient for washing the private parts of a human body.

4 Claims, 3 Drawing Figures

FIG.1
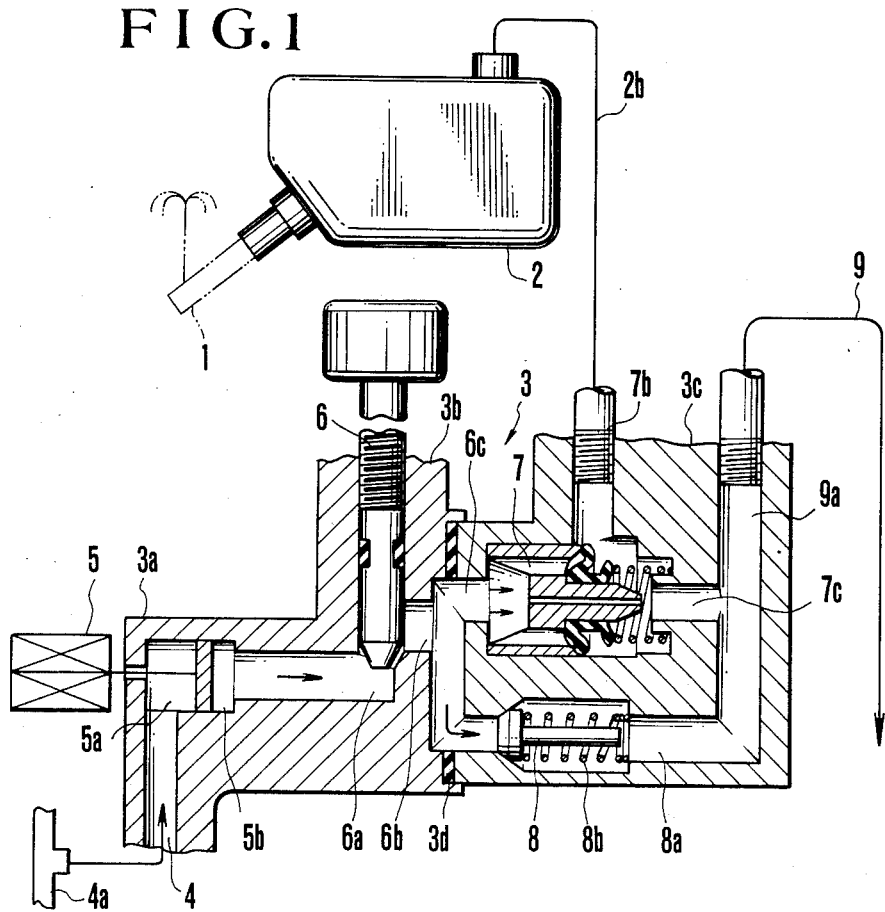
FIG.2
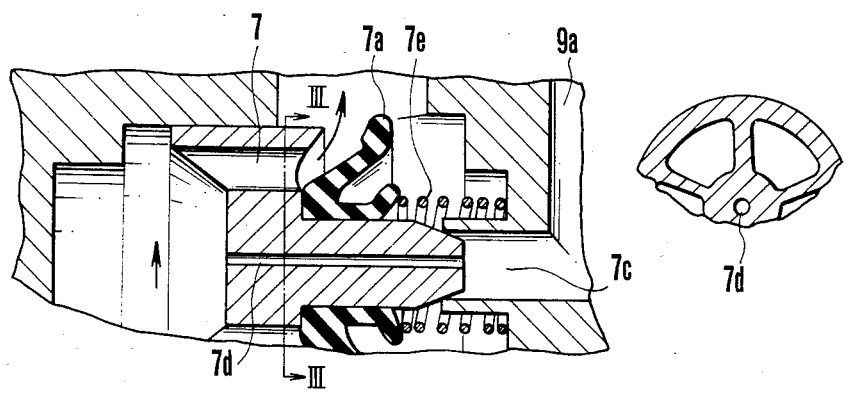
FIG.3

VALVE UNIT FOR A WASHING DEVICE OF PRIVATE PARTS OF HUMAN BODY

BACKGROUND OF THE INVENTION

1. Field of the Invention

This invention relates to an improved water flow control valve unit for a washing device of the private parts of a human body.

2. Prior Art

In the device for washing the private parts of a human body using a nozzle for spouting water, the nozzle is often so arranged that it moves to a position for use against spring force, and after use, is forced to return to the original position by restoring force of the spring. The washing device of this type is sometimes provided with a changeover valve which is used for supplying water to a warm water tank during use, and for draining out warm water remaining in the nozzle after use. The changeover valve of this type is disclosed, for example, in the Japanese Utility Model Publication No. 56-3415 (No. 3415/1981). In that device, the changeover valve is arranged in a valve room formed in the upper portion of the warm water tank. The valve body of the changeover valve has an orifice through which water is supplied into the tank during use. However, in the device of this type, the diameter of the orifice cannot but be limitted owing to the limitted space of the valve room. Consequently, the water pressure given to the warm water tank by the water supplied to the tank through the changeover valve becomes sometimes insufficient. This in turn makes the pressure of the warm water spouting out of the nozzle to be insufficient for washing the private parts of the human body.

Moreover, in the washing device of the above type, several kinds of valve are equipped separately in different portions of the device. For instance, the opening-closing valve for supplying water to the washing device, the valve for regulating the water quantity and the changeover valve are equipped separately at the supplying side of each portion; and the relief valve for protecting the device in case of unusual high water pressure are equipped unitedly to the warm water tank. In case of such arrangement of valves, a water-sealing structure is necessary for each portion where the valve is equipped, that is, many portions of the device must have a water sealing structure. This causes the increase of numbers of parts of device and the numbers of process for assemblying the device.

SUMMARY OF THE INVENTION

The object of the present invention is to provide an improved valve unit for the washing device of the private parts of a human body, which can maintain the pressure of warm water spouting from the nozzle at a degree sufficient to wash the private parts of a human body.

In accordance with the present invention, the valve body of the changeover valve has a plurality of longitudinal holes for passing water, along the inside of the circumference of the valve body. The valve body is further equipped with a diaphragm of which the outer or inner circumferential portion is secured to the valve body. The diaphragm opens only when water passes through said holes during the use of the washing device, and after finishing the wash, closes the holes in order to prevent the counter flow of water into the holes. The area of the diaphragm for receiving the counter flow can be free from the diameter of the holes. Consequently, by making the diameter of holes to be as large as possible, unwanted decrease of the pressure of water spouting from the nozzle of the device is prevented. Moreover, the extention of the time for returning the valve body to the original position and for draining water is prevented by making the pressure-receiving area to be large even when the holes have large diameters.

Another object of the present invention is to provide an improved valve unit for the washing device of the private parts of a human body, which has a simplified and efficient water-sealing structure and can be assembled with a simplified process, by decreasing the numbers of sealed position of the device. Namely, in the washing device according to the present invention, there is provided a valve unit incorporating several valve means necessary for the washing device. The opening-closing valve, the flow controlling valve, the relief valve and the changeover valve are all arranged in this valve unit concentratedly. By this arrangement of valves, the whole structure of the washing device can be a compacted one and numbers of sealed portion can be decreased. Moreover, by setting the relief valve at a position before the water supplying pipe to the warm water tank, the tank and the water supplying pipe to the tank are protected from an unusual high pressure of supplied water.

The foregoing and other objects, features and advantages of the present invention will be understood more clearly and fully from the following detailed description of preferred embodiments with reference to the attached drawings.

BRIEF DESCRIPTION OF THE DRAWINGS

FIG. 1 is an outline of the sectional view of one embodiment of the washing device of the present invention.

FIG. 2 is an enlarged sectional view of the changeover valve portion in FIG. 1.

FIG. 3 is a sectional view of the valve body at III-⇄III line in FIG. 2.

PREFERRED EMBODIMENT OF THE INVENTION

Refering to FIG. 1 through FIG. 3, the nozzle 1 for washing the private parts of a human body by the water spouting therefrom, is equipped in the warm water tank 2. The nozzle is so arranged that it can move slidably forward and backward according to the pressure of warm water as in a device Japanese Utility Model Publication No. 56-3415 (No. 3415-1981). The valve unit 3 connected to the pipe 2b for supplying water to the warm water tank 2 comprises the front body 3a, the central body 3b, the rear body 3c and sealed portion 3d. The front body 3a is connected to a water supplying pipe 4a and includes a water supplying port 4 and a opening-closing valve 5 having the inlet 5a and the outlet 5b. The central body 3b is connected to the front body 3a and includes water quantity regulating valve 6 having the inlet 6a, the outlet 6b and the valve room 6c. The rear body 3c is connected to the central body 3b and includes the changeover valve 7, the relief valve 8 and the drain port 9a. The changeover valve 7 has a small longitudinal center hole 7d and a plurality of the holes 7g which are formed longitudinally and along the inside of the circumference of the valve body. Preferably, holes 7g has a sector-like view and are arranged along the inside of the circumference at regular intervals, as shown in FIG. 3. The diaphragm 7a is closed or opened according to the pressure of water passing through the hole 7g and the force of the spring 7e. The changeover valve 7 communicates with the tank-side outlet 7b and the drain-side outlet 7c. The relief valve 8 is biased leftward in the drawing by the spring 8b. The relief outlet 8a and the drain-side outlet 7c communicates with the drain 7 through the drain port 9a.

In the use of the washing device, water is supplied under pressure from the water pipe 4a to the water supply port 4. By operating the valve 5, the water reaches to the changeover valve 7 and the relief valve 8, through the inlet 5a and the outlet 5b of the water supply port 4 and the inlet 6a and the outlet 6b of the water quantity regulating valve 6.

If the pressure of the supplied water is lower than the operation point of the relief valve 8, the water pushes the changeover valve 7 rightward in the drawing, whereby the drainside outlet 7c is closed and the diaphragm 7a is opened. Consequently, the water runs into the warm water tank 2 through the outlet tankside 7b and the pipe 2b. The water supplied to the warm water tank 2 moves the nozzle 1 forward against the spring force and spouts from the nozzle at a prescribed position. On the contrary, if the water pressure is higher than the operation point of the relief valve 8, the relief valve moves rightward in the drawing, whereby a part of water is released through the relief outlet 8a and drain port 9a. Consequently, the pressure of water supplied to the warm tank 2 is maintained below a prescribed degree.

After the use of the device, the supply of water to the nozzle 1 is ceased by closing the valve 5, thereby the nozzle 1 moves backward by spring force, and consequently, a part of water in the nozzle 1 and the warm water tank 2 is pushed and returns to the tankside outlet 7b through the pipe 2. At this time, the changeover valve 7 moves leftward in the drawing and the water pressure between the changeover valve 7 and the flow control valve 6 is released through the small center hole 7d and the drain 9. Consequently, the tankside outlet 7b and the drainside outlet 7c communicate each other and the water pressure in the tankside outlet 7b and the pipe 2 is released through the drain 9. Thus, the nozzle 1 returns rapidly to the original non-use position.

It should be understood that the preferred embodiments of the present invention have been described herein in considerable detail and that certain modifications, changes and adaptations may be made therein by those skilled in the art and that it is hereby intended to cover all modification, changes and adaptations thereof falling within the scope of the appended claims.

What is claimed is:

1. A water flow control valve unit for a washing device of the private parts of a human body, which provides a washing nozzle movable forward and backward by the pressure of water, comprising;
   first portion connected to the water supplying source and having an opening-closing valve,
   second portion connected to said first portion and having a water quantity regulating valve,
   third portion connected to said second portion and having a changeover valve, a relief valve and a drain port,
   said third portion being further connected to a drain pipe and a pipe for supplying water to a warm water tank having a washing nozzle,
   said changeover valve being so arranged as to send water to the pipe for supplying water to the warm water tank closing the drain port during the use of the washing device, and after the use of the washing device, to send the returning water from the warm water tank to the drain pipe opening the drain port,
   said relief valve being so arranged to release the excessive water pressure between the water quantity regulating valve and the changeover valve, and
   said first portion, second portion and third portion being constituted as a single unit.

2. A valve unit of claim 1, wherein the changeover valve comprises:
   a valve body,
   a small longitudinal hole formed in the center portion of the valve body,
   a plurality of longitudinal holes formed along the inside of the circumference of the valve body, and
   a diaphragm fixed to the valve body and arranged so as to open only when the valve body moves against the spring force being pushed by the water pressure and water passes through said longitudinal holes along the inside of the circumference of the valve body.

3. A valve unit of claim 2, wherein the longitudinal holes formed along the inside of the circumference of the valve body are arranged at regular intervals.

4. A valve unit of claim 3, wherein each of the longitudinal holes has a sector-like sectional view.

* * * * *